(12) United States Patent
Seto et al.

(10) Patent No.: US 8,540,626 B2
(45) Date of Patent: Sep. 24, 2013

(54) ENDOSCOPE BEAM SOURCE APPARATUS AND ENDOSCOPE SYSTEM

(75) Inventors: Yasuhiro Seto, Kanagawa (JP); Hiroshi Murakami, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 160 days.

(21) Appl. No.: 13/182,052

(22) Filed: Jul. 13, 2011

(65) Prior Publication Data
US 2012/0016201 A1 Jan. 19, 2012

(30) Foreign Application Priority Data

Jul. 15, 2010 (JP) ................ P2010-160682

(51) Int. Cl.
*A61B 1/06* (2006.01)
(52) U.S. Cl.
USPC .......................................... 600/178; 600/180
(58) Field of Classification Search
USPC .................. 600/103, 109, 113, 160, 17, 180, 600/181; 362/574; 348/68, 69
See application file for complete search history.

(56) References Cited

U.S. PATENT DOCUMENTS

| | | | |
|---|---|---|---|
| 5,325,383 A * | 6/1994 | Davis et al. ................... | 372/26 |
| 8,232,902 B2 * | 7/2012 | Filippo et al. ................. | 341/54 |
| 2008/0027278 A1 | 1/2008 | Mizuno | |
| 2009/0062617 A1 * | 3/2009 | Mizuyoshi ................... | 600/178 |

FOREIGN PATENT DOCUMENTS

| | | |
|---|---|---|
| JP | 2007-111151 A | 5/2007 |
| JP | 2008-029621 A | 2/2008 |
| JP | 2009-056248 A | 3/2009 |

OTHER PUBLICATIONS

U.S. Appl. No. 13/182,009, filed Jul. 13, 2011.

\* cited by examiner

*Primary Examiner* — Philip R Smith
(74) *Attorney, Agent, or Firm* — McGinn IP Law Group, PLLC

(57) ABSTRACT

The endoscope beam source apparatus includes a beam source for emitting a radiation beam to be supplied to the endoscope, and a beam source control unit for controlling the emission beam intensity of the beam source according to a beam quantity specified value input therein. The beam source control unit specifies the emission beam intensity corresponding to the beam quantity specified value based on at least three of control amounts. The control amounts include a control amount corresponding to pulse number modulation (PNM) control for changing lighting time of the beam source, a control amount corresponding to pulse width modulation (PWM) control for changing a plus width which indicates the lighting or lighting-out time within a control cycle, a control amount corresponding to pulse amplitude modulation (PAM) control for changing the lighting intensity, and a control amount corresponding to pulse density modulation (PDM) control for changing a lighting interval.

6 Claims, 14 Drawing Sheets

ENDOSCOPE BEAM SOURCE APPARATUS AND ENDOSCOPE SYSTEM

CROSS-REFERENCE TO RELATED APPLICATIONS

This application claims the benefit of Japanese Patent Application No. 2010-160682, filed on Jul. 15, 2010, the entire contents of which are hereby incorporated by reference, the same as if set forth at length.

BACKGROUND OF THE INVENTION

1. Technical Field

The present invention relates to an endoscope beam source apparatus and an endoscope system including such apparatus.

2. Description of Related Art

Generally, to observe tissue within a body cavity, there is used an endoscope system. The endoscope system is a system which radiates, as a radiation beam, a white beam onto a portion to be observed within the body cavity, picks up a beam image due to a reflection beam from the portion to be observed using a predetermined imaging device which is capable of imaging a two-dimensional image, and displays the thus obtained two-dimensional image on a monitor screen. A technology for controlling the radiation beam of such endoscope system is disclosed in, for example, JP-2009-056248-A, JP-2007-111151-A and JP-2008-029621-A.

In JP-2009-056248-A, there is disclosed a technology for always obtaining a radiation beam having proper beam quantity and chromaticity. Specifically, there is proposed a technology in which a drive current to be applied to a beam source is caused to change in the form of a pulse and the pulse is controlled in any one of the number, width and amplitude thereof.

In JP-2007-111151-A, there is disclosed a technology for supplying a radiation beam onto a diseased part while controlling the heating of a leading end. Specifically, there is proposed a technology for controlling the lighting/lighting-out of a beam source in a pulse manner and also for adjusting the lighting time of the beam source and the amplitude (intensity) of the pulse.

According to JP-2008-029621-A, there is disclosed a technology which, when imaging a static image using a CMOS image sensor, turns on beam radiation only for a short period of time. Specifically, the charge accumulation operation is started from a state where the radiation is firstly turned off and charges are then reset at the respective pixel positions. Also, when the charges are read out from the respective pixels, the radiation is turned off. According to this technology, it is possible to prevent extra charges from being accumulated due to different timing for reading the charges from the respective pixels.

Here, a beam source apparatus for radiation used in an endoscope system is generally required to have a beam quantity dynamic range of 1:9000 or broader. Realization of such broad beam quantity dynamic range is difficult simply by controlling the amplitude of a current to be applied to the beam source.

Also, besides the control of the current amplitude, as disclosed in JP-2009-056248-A, the radiation beam quantity can also be controlled by carrying out pulse number control and pulse width control on the beam source application current. However, in any one of the pulse number control, pulse width control and pulse amplitude control, a sufficiently large beam quantity dynamic range cannot be obtained when only one of them is applied.

Also, even in the case that a beam source apparatus has multiple kinds of control functions such as the pulse number control, pulse width control and pulse amplitude control disclosed in JP-2009-056248-A, a user must adjust individually the multiple kinds of control quantities which are different in the properties (the relationship between an input value and a beam quantity variation) from each other. Therefore, an operation to adjust the radiation beam quantity to a desired value is very difficult.

Further, in the case that the beam quantity is controlled using the pulse number control, pulse width control and pulse amplitude control, unless the properties of an imaging device to be mounted on an endoscope are taken into consideration, there cannot be obtained an image of high quality.

Here, as an imaging device which can be used in the endoscope system in order to image the two-dimensional image, there are known a CCD (Charge Coupled Device) image sensor and a CMOS (Complementary Metal-Oxide Semiconductor) image sensor. Also, as known well, the signal reading systems of the CCD image and CMOS image sensors are different from each other because they are different in structure, and the two image sensors are also different in the shutter control in photographing.

For example, a CCD image sensor of an interline type includes a beam receiving portion, a vertical transfer portion, a horizontal transfer portion, an amplifier and the like. That is, since the CCD image sensor includes the vertical transfer portion capable of holding charges for all pixels, after completion of exposure, the charges of the beam receiving portion for all pixels can be transferred to the vertical transfer portion at the same timing. Therefore, the timing for starting the accumulation of the charges at the respective pixel positions of the beam receiving portion and the timing for ending the charge accumulation are simultaneous for all pixels. That is, when imaging a two-dimensional image, simply by controlling only the image sensor, the shutter can be released simultaneously for the whole of 1 frame of the two-dimensional image. This shutter control is referred to as a global shutter system.

On the other hand, in the case of an ordinary CMOS image sensor, since there is not provided a structure element such as the above-mentioned vertical transfer portion which can accumulate temporarily the charges of all pixels, it is necessary to read charges sequentially line by line from the respective pixel positions of a beam receiving portion of a two-dimensional arrangement constituted of N lines and M rows. That is, as in the screen scan of a TV set, while switching scan lines sequentially, charges are read out for every line. Therefore, the timing for starting the accumulation of the charges at the respective pixel positions of the beam receiving portion and the timing for ending the charge accumulation vary slightly in every line. In other words, when imaging a two-dimensional image, simply by controlling only the image sensor, timing for releasing the shutter varies in every line of the two-dimensional image, whereby the shutter cannot be released simultaneously for the whole of 1 frame. This shutter control is referred to as a rolling shutter system.

Therefore, in the case of an endoscope system employing an ordinary CMOS image sensor, the timings in the charge accumulation period (the time during which the shutter is substantially opened) at the respective positions of the beam receiving portion is different every scan line. Therefore, in the case that the on start timing of the beam source is adjusted in order to control the radiation beam, the radiation beam quantity varies every scan line of the two-dimensional image, thereby causing the luminance of the image to vary.

In the case that only the amplitude (beam emission intensity) of a current to be supplied to the beam source is controlled, since the radiation beam quantity is not influenced by the difference of the timings for signal reading or the like, even in an endoscope system employing an ordinary CMOS image sensor, there is no possibility that the luminance can vary every scan line.

On the other hand, in an endoscope system employing a CCD image sensor, since the timings for signal reading and the like is not different every scan line, the on start timings of the beam source can also be adjusted in order to control a beam for radiation. Also, in an endoscope system employing a CCD image sensor, since there exists the time during which the shutter is closed simultaneously for all pixels, during this time, unnecessary radiation can be turned off, which is useful in controlling heat generation. However, in an endoscope system employing an ordinary CMOS image sensor, since the time during which the shutter is closed varies every scan line, radiation cannot be turned off during a specific period.

SUMMARY

As described above, according to the type of an imaging device mounted on an endoscope used, the optimum control of the radiation beam varies. However, conventionally, there has not been proposed a technology for optimally controlling the emission beam quantity of a radiation beam according to the type of the imaging device.

Thus, it is an object of the invention to provide an endoscope beam source apparatus which, by controlling the quantity of a radiation beam according to the type of the imaging device of an endoscope used, can obtain a desired beam quantity simply and in a broad beam quantity dynamic range, and an endoscope system including such apparatus.

The present invention is constituted of the following features.

An endoscope beam source apparatus is connected to an endoscope. The endoscope mounts a radiation optical system for radiating a beam onto a subject and an imaging optical system including an imaging device for imaging an image of the subject. The endoscope beam source apparatus includes a beam source and a beam source control unit. The beam source emits radiation beam to be supplied to the endoscope. The beam source control unit controls emission beam intensity of the beam source according to a beam quantity specified value input therein. The beam source control unit specifies the emission beam intensity of the beam source corresponding to the beam quantity specified value based on at least three of control amounts. The control amounts include a control amount corresponding to pulse number modulation control for changing lighting time of the beam source, a control amount corresponding to pulse width modulation control for changing a pulse width which indicates the lighting time or lighting-out time within a control cycle, a control amount corresponding to pulse amplitude modulation control for changing lighting intensity; and a control amount corresponding to pulse density modulation control for changing a lighting interval.

According to the endoscope beam source apparatus of the invention and an endoscope system including such apparatus, since the radiation beam is controlled by integrating the combinations of three or more kinds of modulation control, there can be easily obtained a broad beam quantity dynamic range. Also, since the respective control amounts of the three or more kinds of modulation control can be controlled simply by operating a beam quantity specified value, an operation for a user to perform for the beam control can be simplified greatly.

DETAILED DESCRIPTION OF EMBODIMENTS OF THE INVENTION

Now, description will be given below specifically of an embodiment according to the invention with reference to the accompanying drawings.

Figure 1:
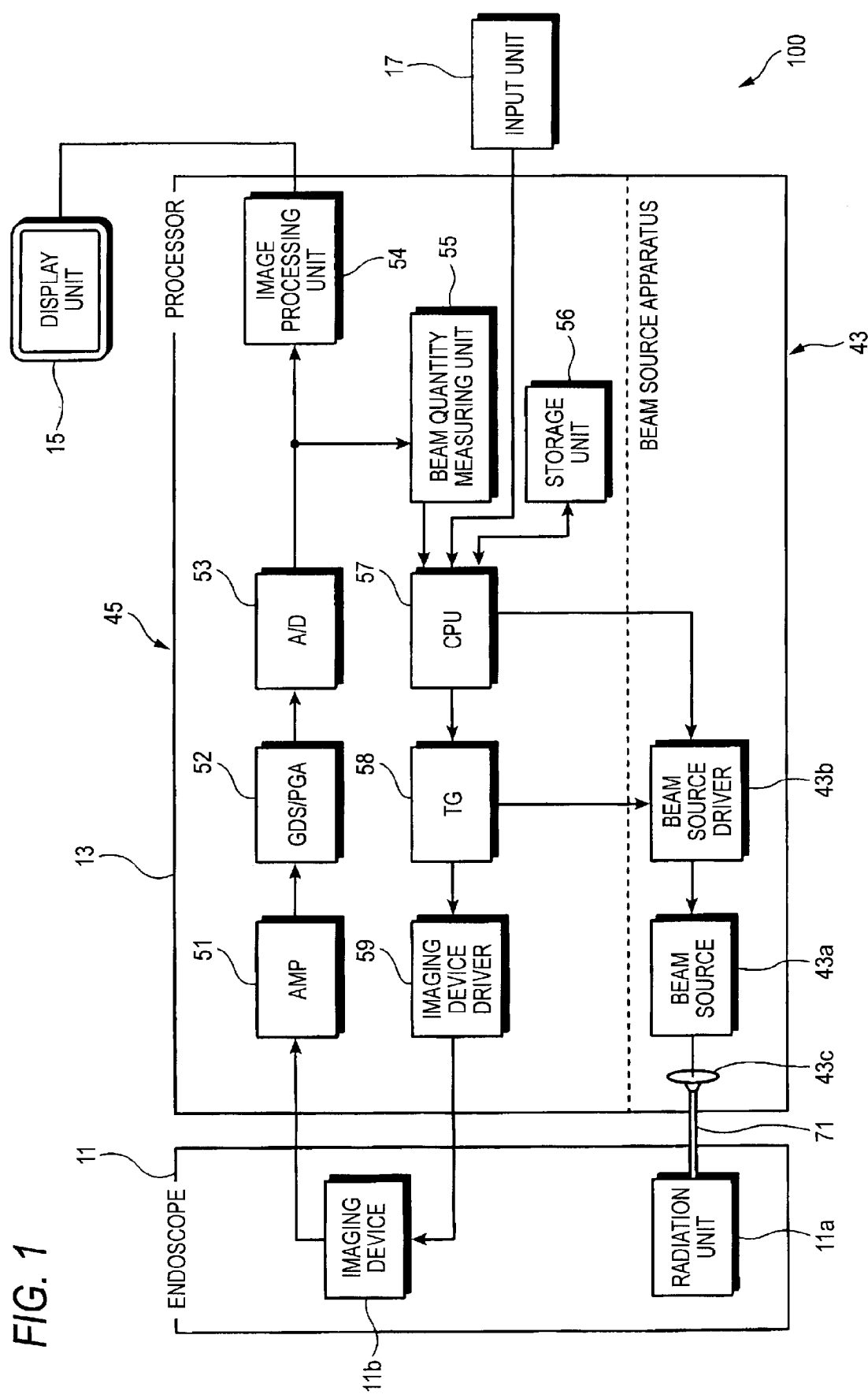
FIG. 1 is a block diagram of an example of the structure of the main portions of the whole of an endoscope system according to an embodiment of the invention.

An example of the structure of the main portions of the whole endoscope system according to the present embodiment is shown in FIG. 1. Also, the appearance of the endoscope system shown in FIG. 1 is shown in FIG. 2.

Figure 2:
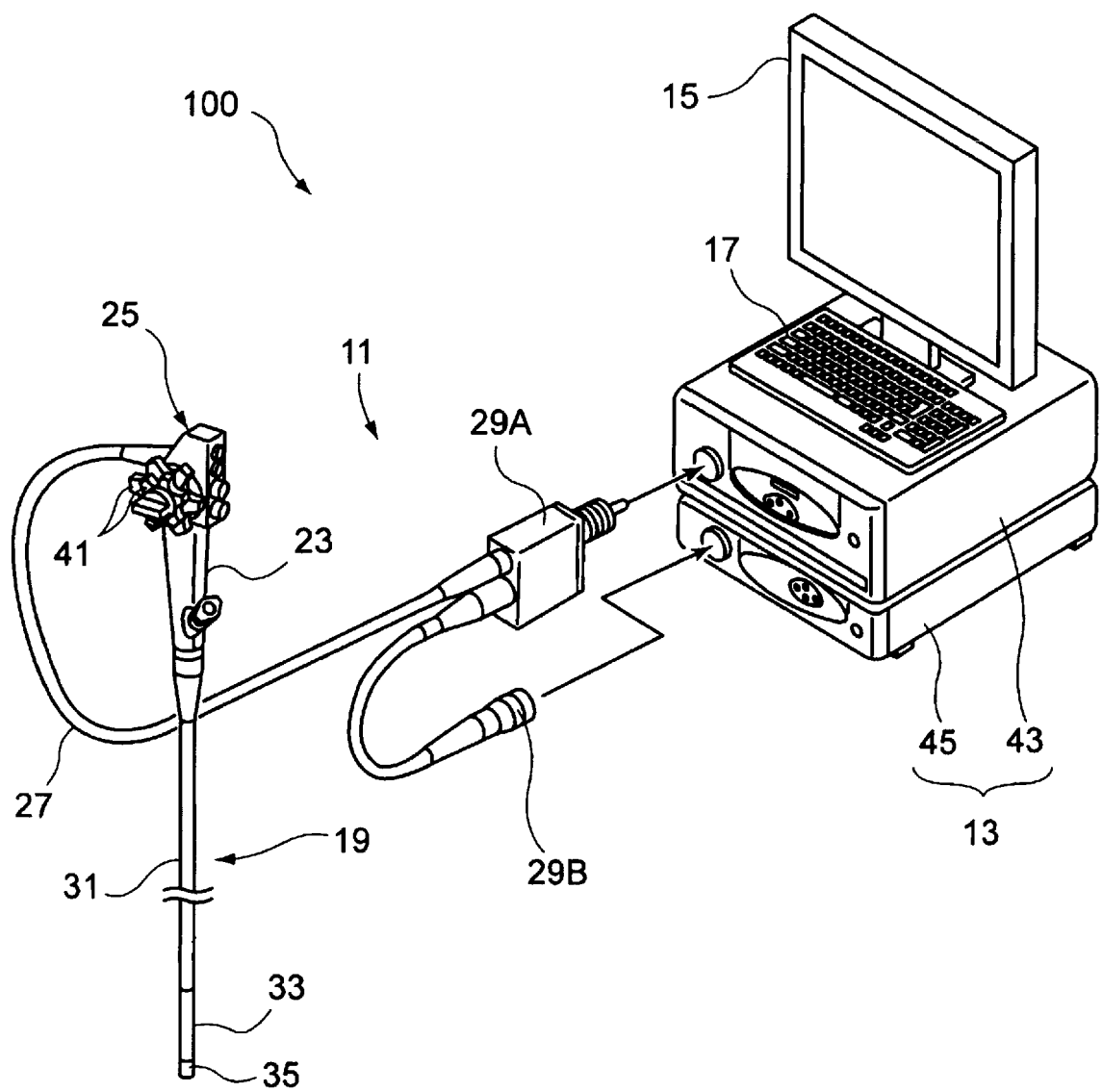
FIG. 2 is a perspective view of the appearance of the endoscope system shown in FIG. 1.

As shown in FIGS. 1 and 2, an endoscope system 100 includes an endoscope 11, a control unit 13 as an external control unit to which the endoscope 11 can be connected, and a display unit 15 connected to the control unit 13 for displaying image information. And, an input unit 17 is connected to the control unit 13 for accepting an input operation.

The endoscope 11 is an electronic endoscope which, as shown in FIG. 1, includes a radiation unit 11a (a radiation optical system) and an imaging device 11b (an imaging optical system). The radiation unit 11a emits a radiation beam from the leading end of an endoscope insertion unit 19 shown in FIG. 2. The imaging device 11b is a two-dimensional imaging device which can pick up the image of an area to be observed of a living body or the like through a certain object lens unit to thereby obtain a two-dimensional image. As a specific example of the imaging device 11b, there can be used a two-dimensional CCD (Charge Coupled Device) image sensor or a two-dimensional CMOS (Complementary Metal-Oxide Semiconductor) image sensor.

Here, in the endoscope system 100, normally, it is necessary to reproduce a color image. Thus, as the imaging device 11b, actually, there is used an imaging device of a single plate color imaging optical system including a color filter (for example, a Bayer-arranged RGB original color filter, or a CMYG, CMY complementary color filter) constituted of multiple color segments.

The endoscope 11, as shown in FIG. 2, includes an endoscope insertion unit 19, an operation unit 25, a universal code 27, and connector units 29A & 29B. The endoscope insertion unit 19 is formed to have a long and narrow shape and the leading end side thereof can be inserted into a subject. Also, the endoscope insertion unit 19 is constituted of a flexible soft portion 31, a curved portion 33 and a leading end portion (which is also hereinafter referred to as an endoscope leading end portion). The operation unit 25 is connected to the base end portion of the endoscope insertion unit 19 and is used to perform the curving operation of the leading end of the endoscope insertion unit 19 and an operation for observation. The universal code 27 is extended from the operation unit 25. The connector units 29A and 29B are respectively provided on the leading end of the universal code 27 and are used to connect the endoscope 11 to the control unit 13 removably.

The curved portion 33 is interposed between the soft portion 31 and endoscope leading end portion 35 and can be curved by rotating an angle knob 41 provided on the operation unit 25. The curved portion 33 can be curved in an arbitrary direction and at arbitrary angle according to the portion of the subject to which the endoscope 11 is applied, thereby being able to set the radiation direction of the radiation window for radiation of the endoscope leading end portion 35 and the observation direction of the imaging device to a desired observation portion.

Figure 3:
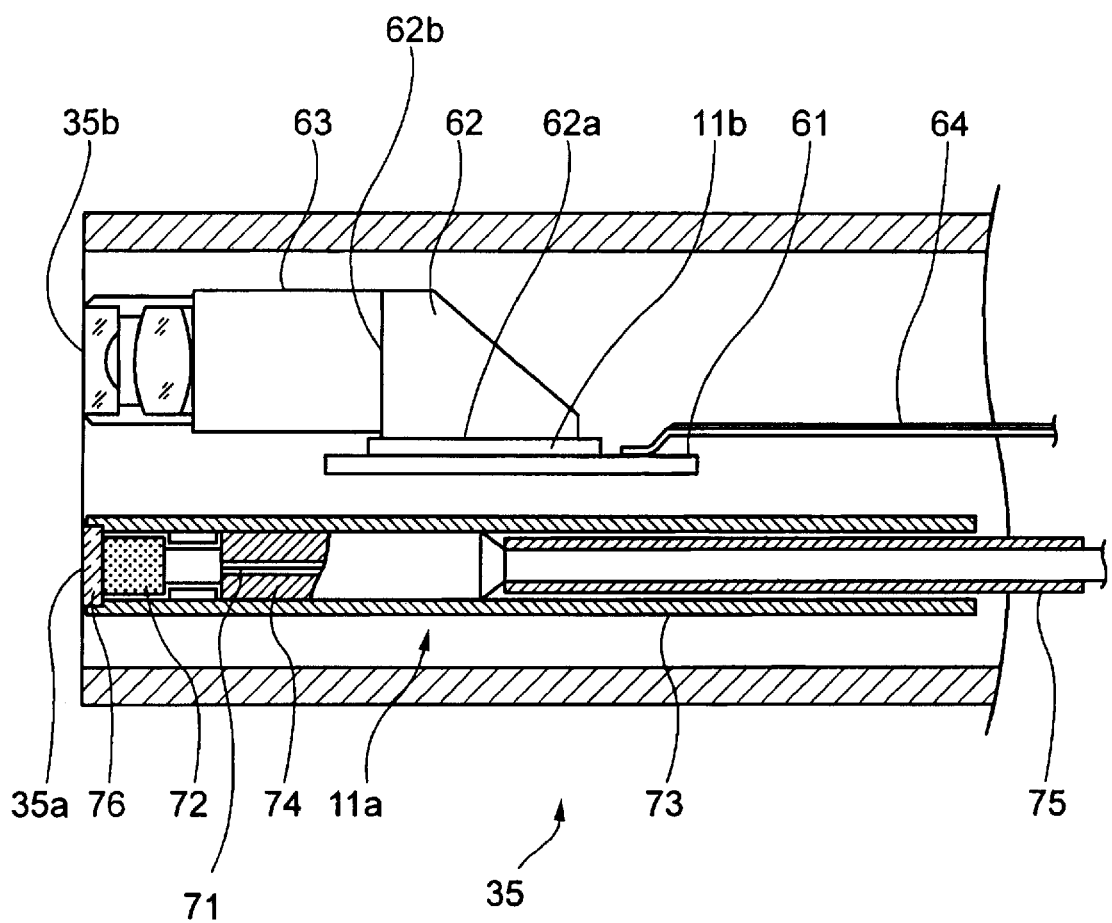
FIG. 3 is a longitudinal section view of the neighboring structure of the leading end portion of an endoscope.

FIG. 3 shows the structure of the neighboring portion of the endoscope leading end portion 35. As shown in FIG. 3, in the endoscope leading end portion 35, there are formed a radiation unit 11a for radiating a radiation beam onto the area to be observed and an imaging device 11b for imaging the image of the area to be observed.

The radiation unit 11a includes a multi-mode optical fiber 71 and a fluorescent member 72. As the multi-mode optical fiber 71, for example, there can be used a small diameter optical fiber which has a core diameter of 10 μm, a clad diameter of 125 μm, and a diameter of 0.3 mm~0.5 mm when including a protection layer serving as a coating.

The multi-mode optical fiber 71 guides a blue beam, which is emitted from a beam source 43a disposed within a beam source apparatus 43, to the vicinity of the fluorescent member 72 of the endoscope leading end portion 35. The fluorescent member 72 absorbs part of the energy of the blue beam guided by the multi-mode optical fiber 71 and is thereby excited to generate a visible beam having a wavelength band ranging from green~yellow. The fluorescent member 72 is made of plural fluorescent materials; and, for example, it may include a YAG system fluorescent member or a fluorescent material such as AM ($BaMgAl_{10}O_{17}$).

As shown in FIG. 3, there is provided a cylindrical sleeve member 73 in such a manner that it covers the outer periphery of the fluorescent member 72. Into the sleeve member 73, there is inserted a ferrule 74 which is used to hold the multi-mode optical fiber 71 in such a manner that it serves as the center shaft of the multi-mode optical fiber 71. Further, into such portion of the multi-mode optical fiber 71 as is extended from the rear end side (which is opposite to the leading end side) of the ferrule 74, there is provided a flexible sleeve 75 for covering the coating of the multi-mode optical fiber 71 in such a manner that it is interposed between the sleeve member 73 and the multi-mode optical fiber 71.

An emission beam which is generated in the fluorescent member 72 due to excitation and part of the blue beam which is guided by the multi-mode optical fiber 71 and which is transmitted through the fluorescent member 72 are combined together, and the thus combined beam is emitted from the radiation window 35a toward the area to be observed as a radiation beam having a spectrum near white. In the vicinity of the radiation window 35a, a radiation lens 76 is provided for radiating the radiation beam.

As shown in FIG. 3, the imaging device 11b is disposed on a base plate 61 which is fixed to the inside of the endoscope leading end portion 35. Also, to the beam receiving surface of the imaging device 11b, there is connected one end face 62a of a prism 62. And, to the other end face 62b extending at right angles to the end face 62a, there is connected an object lens unit 63. In order to be able to pick up the image of the area to be observed from an observation window 35b which is formed to face the area to be observed, the object lens unit 63 guides its beam to the beam receiving surface of the imaging device 11b through the prism 62. A signal cable 64 is used to connect the imaging device 11b on the base plate 61 to the control unit 13 electrically.

As shown in FIG. 1, the control unit 13 is constituted of a processor 45 and a beam source apparatus 43. The beam source apparatus 43 is used to emit a radiation beam to be supplied to the radiation window of the endoscope leading end portion 35. The processor 45 functions a beam controller which image processes an image signal to be output from the imaging device 11b and also controls the beam quantity for radiation. The processor 45 and beam source apparatus 43, as shown in FIG. 2, are respectively connected to the endoscope 11 through the connector units 29A and 29B.

Also, to the processor 45, there are connected the above-mentioned display unit 15 and input unit 17. The processor 45, according to an instruction from the operation unit 25 or input unit 17 of the endoscope 11, image processes an imaging signal transmitted from the endoscope 11, generates a display image and supplies it to the display unit 15.

Next, description will be given below of the signal processing of the endoscope system.

As shown in FIG. 1, the processor 45 includes an amplifier (AMP) 51, a correlated double sampling/programmable gain amplifier (which is hereinafter referred to as CDS/PGA) 52, an A/D converter 53, an image processing unit 54, a beam quantity measuring unit 55, a storage unit 56, a microcomputer (CPU) 57, a timing generator (TG) 58, and an imaging device driver 59.

To the input of the amplifier 51, there is input an imaging signal which can be obtained through the photographing of the imaging device 11. After the imaging signal is amplified by the amplifier 51 having a constant gain, it is input to CDS/PGA 52. CDS/PGA 52 inputs therein an imaging signal amplified by the amplifier 51 and outputs it as an analog image signal representing the levels of the respective colors, that is, R (red), G (green) and B (blue) respectively correspondingly accurately to the accumulated electric charges of the respective photoelectric conversion cells of the imaging device 11b.

The analog image signal output from CDS/PGA 52 is input to the A/D converter 53, where it is converted to digital image data. The image processing unit 54 performs various image processings on the digital image data output from the A/D converter 53 to generate information about the image to be displayed on the screen of the display unit 15. Therefore, on the display unit 15, there is displayed an image picked up by the imaging device 11b of the endoscope 11, that is, the two-dimensional image of the area to be observed of a living body.

To a control input terminal used to control the photographing of the imaging device 11b and signal read-out, there is connected the output of the imaging device driver 59. Also, to the input of the imaging device driver 59, there is connected the output of the timing generator 58. The imaging device driver 59, using various timing signals (clock pulses) input from the timing generator 58, controls various kinds of timing in the photographing of the imaging device 11b. That is, it controls timing for reading out signal charges accumulated in the respective cell areas through the photographing and the shutter speed of an electronic shutter. The timing generator 58 also generates a timing signal which is given to the beam source driver 43b.

In the processor 45 according to the present embodiment, in order that, according to the type of the imaging device 11b of an endoscope to be connected to the processor 45, there can be output a timing signal necessary to perform a desired photographing operation, there is included a timing generator 58. That is, when the imaging device 11b of an endoscope to be connected is of a global shutter system, the timing generator 58 outputs a timing signal for a global shutter system; and, when the element 11b is of a rolling shutter system, the timing generator 58 outputs a timing signal for a global shutter system. Or, the timing generator 58 may also be structured such that it can be switched to any one of the two shutter systems.

That is, for a CCD image sensor of a global shutter system, exposure operations for the respective cells of all pixels are performed simultaneously, whereas, for an ordinary CMOS image sensor of a rolling shutter system, while varying timing for every scan line (line by line), the exposure and signal reading operations must be performed sequentially. Here, a CMOS image sensor may be of a global shutter system and, in this case, it may be treated similarly to a CCD image sensor of a global shutter system. The timing generator 58 according to the present embodiment is structured such that it corresponds to any one of the two shutter systems. However, it may also be structured such that it can correspond to both shutter systems selectively.

The beam quantity measuring unit 55 measures a beam quantity according to the digital image data output from the A/D converter 53. For example, it detects the maximum luminance, minimum luminance, average luminance and the like of the whole area from the digital image data output obtained by photographing to thereby be able to determine whether an image having desired brightness has been picked up or not.

In the storage unit 56, there are previously stored one or a plurality of control patterns to be instructed to the beam source driver 43b for beam control. This control pattern is taken out and is transmitted to the beam source driver 43b. Here, this control pattern may also is stored in the beam source driver 43b previously.

The microcomputer 57 executes a previously predetermined program to thereby control the whole of the endoscope system 100. Typical processings to be executed under the control of the microcomputer 57 are as follows.

1. The imaging device driver 59 provides an instruction to the timing generator 58 so as to drive the imaging device 11b according to a global shutter system or a rolling shutter system.

2. According to an instruction on a shutter speed and the like input from the input unit 17 based on the operation of a user, the microcomputer 57 provides another instruction to the timing generator 58. The instruction indicates that the imaging device driver 59 should drive the imaging device 11b at the instructed shutter speed.

3. The microcomputer 57 provides an instruction to the beam source apparatus 43 such that the beam source apparatus 43 should control the beam quantity according to a beam quantity specified value for radiation control, which is determined by a beam quantity measured by the beam quantity measuring unit 55 or by a specified value input from the input unit 17, and according to a predetermined control pattern.

As shown in FIG. 1, the beam source apparatus 43 includes a beam source 43a, a beam source driver 43b and a condenser lens 43c. In the case that the beam source 43a is electrically energized under the control of the beam source driver 43b, the beam source 43a generates a beam and emits this beam therefrom. This beam is condensed by the condenser lens 43c and is then guided into an optical fiber 71. And, the beam is transmitted through the optical fiber 71 and is then guided to the radiation unit 11a.

Here, according to the present embodiment, as the beam source 43a, there is used a blue LED (light emitting diode) having an oscillation wavelength of 405 nm or 445, or an LD (laser diode), for example, an InGaN system laser diode of a broad area type, an InGaNAs system laser diode, or a GaNAs system laser diode.

The beam source driver 43b is connected to the timing generator 58 and microcomputer 57 of the processor 45. The beam source driver 43b, according to an instruction provided from the microcomputer 57 and the timing of a signal input therein from the timing generator 58, supplies a pulse-shaped drive current to the beam source 43a. The beam source driver 43b is structured such that it corresponds to a global shutter system or a rolling shutter system. Alternatively, the beam source driver 43b may also include both structures and thus one of the structures may be used selectively.

Figure 4:
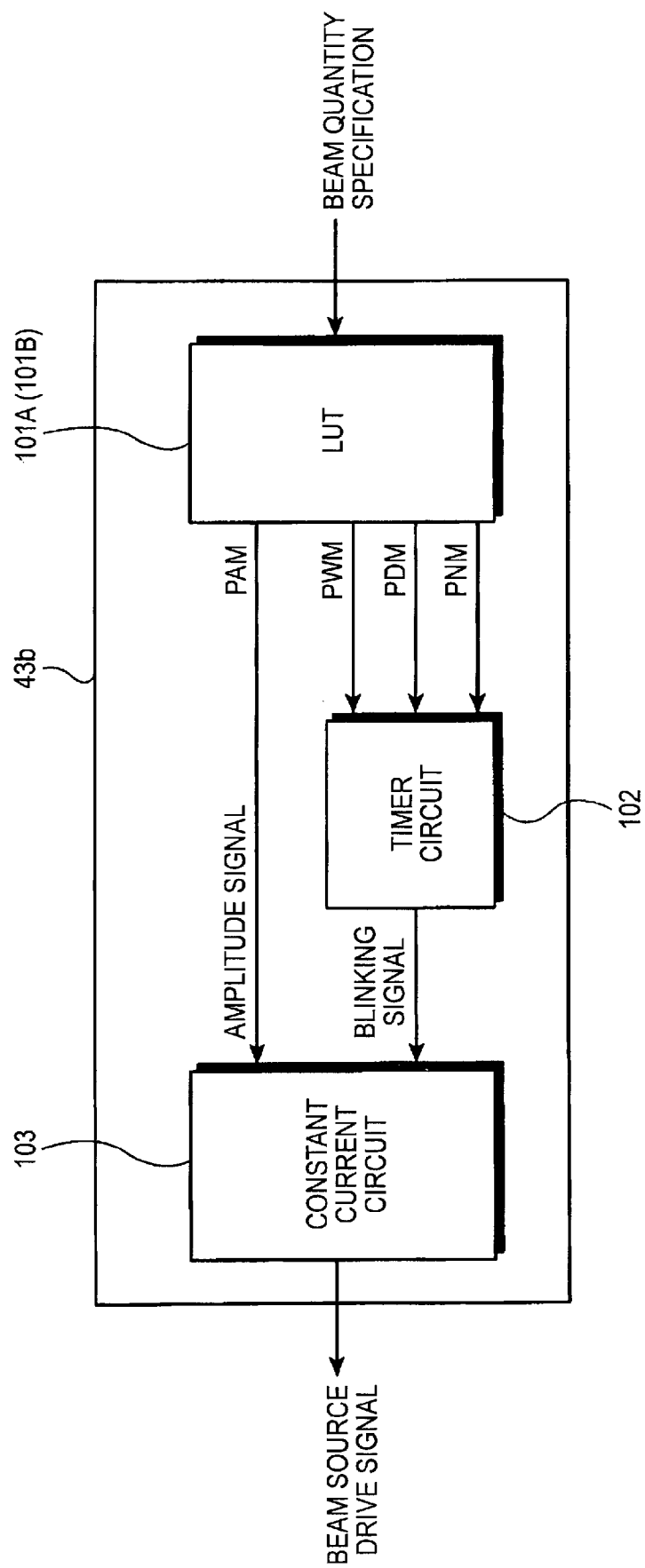
FIG. 4 is a block diagram of a specific example of the structure of a beam source driver.

A specific example (1) of the structure of the beam source driver 43b is shown in FIG. 4. The beam source driver 43b having the structure shown in FIG. 4 is used to perform electronic shutter control according to a global shutter system. That is, in the case that there is connected the endoscope 11 on which a CCD image sensor is mounted as the imaging device 11b, the beam source driver 43b having the structure shown in FIG. 4 is mounted onto the beam source apparatus 43. According to the example shown in FIG. 4, the beam source driver 43b includes an LUT (look-up table) 101A, a timer circuit 102 and a constant current circuit 103.

This beam source driver 43b combines three kinds of control, that is, pulse number modulation (PNM) control, pulse width modulation (PWM) control and pulse amplitude modulation (PAM) control to generate a beam source drive signal for controlling the current of the beam source 43a. The contents of the respective PAM, PWM and PNM control will be described later.

In LUT 101A, there are stored combinations of the respective control values of PAM, PWM and PNM control corresponding to specified beam quantities as control patterns. The control patterns stored in LUT 101A are used to specify the emission beam intensity of the beam source 43a corresponding to the beam quantity specified values as a combination of three control amounts, that is, a control amount corresponding to pulse number modulation (PNM) control, a control amount corresponding to pulse width modulation (PWM) control and a control amount corresponding to pulse amplitude modulation (PAM) control. Since the beam source is controlled by combining the multiple kinds of control in this manner, the dynamic range of the emission beam quantity of the beam source can be enlarged.

The timer circuit 102, according to the respective control values of PWM and PNM control input from LUT 101A and the timing of a signal input from the timing generator 58, gives the constant current circuit 103 a blinking signal for supplying a pulse-shaped drive current to the beam source 43a.

The constant current circuit 103, according to an amplitude signal corresponding to the control value of PAM control input from LUT 101A and the blinking signal output from the timer circuit 102, generates a beam source drive signal for controlling the current of the beam source 43a.

Another example (2) of the structure of the beam source driver 43b is similar to the structure shown in FIG. 4, whereas an LUT is an LUT 101B for a rolling shutter system. In this case, the beam source driver 43b is used to perform electronic shutter control according to a rolling shutter system. That is, in the case that there is connected an endoscope 11 on which a CMOS image sensor is mounted as the imaging device 11b, the beam source driver 43b including the LUT 101B shown in FIG. 4 is mounted onto the beam source apparatus 43. In this example, the beam source driver 43b includes an LUT (look-up table) 101B, a timer circuit 102 and a constant current circuit 103.

Also, this beam source driver 43b combines three kinds of control, that is, pulse density modulation (PDM) control, pulse width modulation (PWM) control and pulse amplitude modulation (PAM) control to generate a beam source drive signal for controlling the current of the beam source 43a. The contents of the respective PDM, PWM and PNM control will be described later.

In LUT 101B, there are stored combinations of the respective control values of PDM, PWM and PNM control corresponding to specified beam quantities as control patterns. The control patterns stored in LUT 101B are used to specify the emission beam intensity of the beam source 43a corresponding to the beam quantity specified value as a combination of three control amounts, that is, a control amount corresponding to pulse density modulation (PDM) control, a control amount corresponding to pulse width modulation (PWM) control and a control amount corresponding to pulse amplitude modulation (PAM) control. In this case as well, since the beam source is controlled by combining the multiple kinds of control, the dynamic range of the emission beam quantity of the beam source can be enlarged.

The timer circuit 102, according to the respective control values of PWM and PDM control input from LUT 101B and the timing of a signal input from the timing generator 58, gives the constant current circuit 103 a blinking signal for supplying a pulse-shaped drive current to the beam source 43a.

In this case, the constant current circuit 103, according to an amplitude signal corresponding to the control value of PAM control input from LUT 101B and the blinking signal output from the timer circuit 102, generates a beam source drive signal for controlling the current of the beam source 43a.

Here, LUTs 101A and 101B, as described above, are respectively structured such that they store the respective control amounts as tables. However, they may also be structured such that they can obtain the respective control amounts according to an operation equation.

Figure 5:
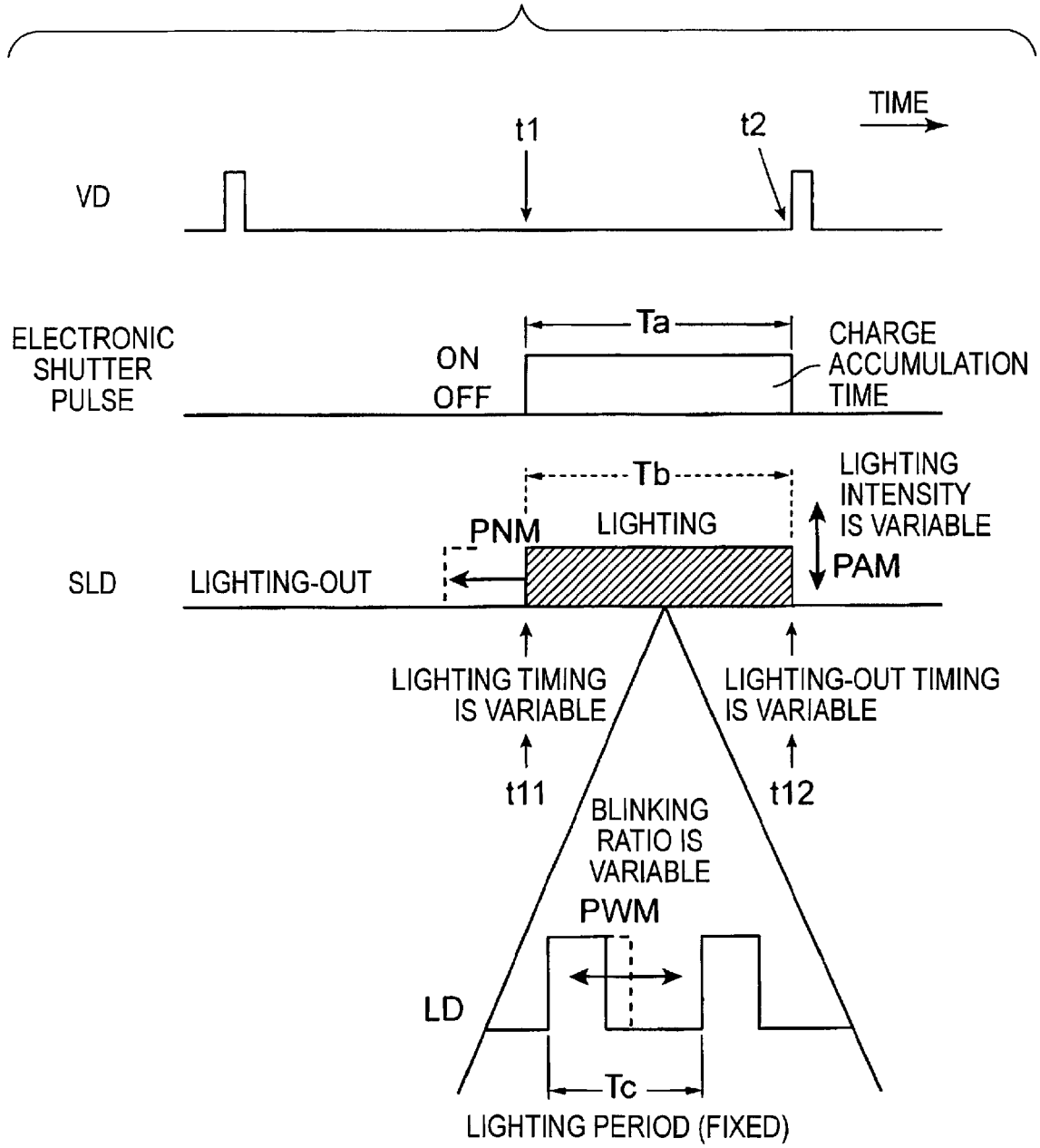
FIG. 5 is a time chart of an example of control timing when controlling the quantity of a radiation beam according to a global shutter system.

FIG. 5 shows an example of control timing in a case where the electric charge accumulation period of the photoelectric conversion portion of the imaging device is controlled by an electronic shutter of a global shutter system, as in a case where the imaging device 11b of the endoscope 11 connected to the control unit 13 is an image sensor of a CCD type.

In FIG. 5, there are shown a vertical scan signal VD for controlling the scan of the imaging device 11b, an electronic shutter pulse, and the drive signal SLD (corresponding to the beam source drive signal shown in FIG. 4) of the laser diode LD serving as the beam source for radiation (corresponding to 43a shown in FIG. 1). Also, in the vertical scan signal VD shown in FIG. 5, the duration between one pulse and next pulse represents the time of 1 screen (1 frame).

And, during the lighting time (Ta) of the electronic shutter pulse, in such area of a cell as corresponds to each pixel of the photoelectric conversion portion of the imaging device 11b, electric charges are generated and accumulated, which corresponds to the received beam intensity and exposure time (corresponding to Ta) by a photo diode or the like. In this case, since the electronic shutter employs a global shutter system, the electric charges of all pixels are accumulated at the same timing. That is, in each of a large number of pixels, the charge accumulation starts at the time t1 shown in FIG. 5 and ends at the time t2 when the time passes the time Ta of the electronic shutter.

Since radiation in this case has no influence on the image to be picked up except for the time when the electronic shutter is opened, the beam source drive signal SLD for controlling the radiation beam is controlled to turn on the beam source in such a manner that its turn-on-timing is so adjusted as to synchronize with the timing (t1~t2) of the charge accumulation of the imaging device 11b.

FIG. 5 shows an example in which there is used the beam source driver 43b having a structure including LUT 101A shown in FIG. 4, that is, an example in which the beam quantity for radiation is controlled according to the combinations of the pulse number modulation (PNM) control, pulse width modulation (PWM) control and pulse amplitude modulation (PAM) control.

That is, the time t11 for switching the beam source drive signal SLD shown in FIG. 5 from lighting-out (low level) to lighting (high level) is changed to around the time t1 for opening the electronic shutter, whereby the length of the lighting time Tb can be adjusted, thereby being able to control the beam amount. The time t12 for switching the beam source drive signal from lighting to lighting-out is fixed to the same timing as the time t2. The lighting time Tb is controlled to integer multiples of the lighting-cycle Tc of the PWM control. This is PNM control. Here, the lighting time Tb is set at a ratio which is larger than a predetermined ratio with respect to the charge accumulation time Ta per frame. For example, in the case that the predetermined ratio is set for 1/2, a discontinuous feeling in the moving image reproduction can be prevented and the occurrence of blinking can also be prevented.

Also, even during the lighting time Tb from time t11 to t12 shown in FIG. 5, at every a certain lighting-cycle Tc (for example, about 1/100 of Tb) which is very short, the on/off of the beam source drive signal SLD is controlled to repeat lighting and lighting-out alternately. And, during the respective periods of the lighting-cycle Tc, the width of a pulse representing the time for actually turning on the signal SLD is adjusted. The beam quantity (blinking ratio) is controlled in this manner. This is PWM control.

Also, since the amplitude of the pulse (during t11 and t12) of the beam source drive signal SLD is variable, the intensity (instantaneous value) of the current to be applied to the beam source can be changed, thereby being able to adjust the lighting intensity of the beam source. This is PAM control.

Figure 6:
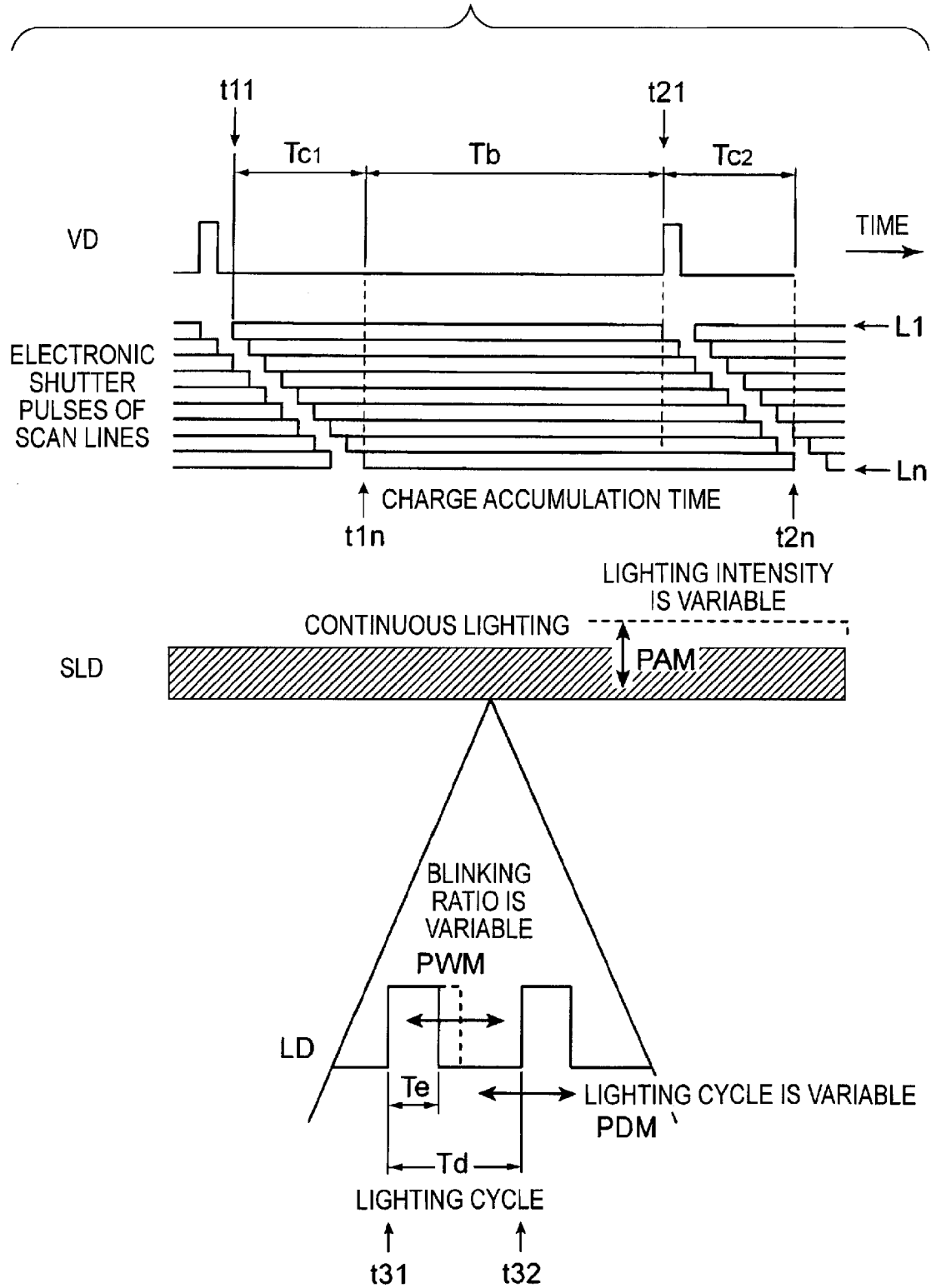
FIG. 6 is a time chart of an example of control timing when controlling the quantity of a radiation beam according to a rolling shutter system.

FIG. 6 shows an example of control timing in which the imaging device 11b of the endoscope 11 connected to the control unit 13 is an ordinary image sensor of a CMOS type and the charge accumulation time of the photoelectric conversion portion of the imaging device is controlled by an electric shutter of a rolling shutter system.

FIG. 6 shows an example in which there is used the beam source driver 43b having a structure including LUT 101B shown in FIG. 4, that is, an example in which the beam quantity for radiation is controlled according to the combinations of the pulse density modulation (PDM) control, pulse width modulation (PWM) control and pulse amplitude modulation (PAM) control.

In FIG. 6, there are shown a vertical scan signal VD for controlling the scan of the imaging device 11b, electronic shutter pulses to be applied to each of a large number of scan lines, and the drive signal SLD (corresponding to the beam source drive signal shown in FIG. 4) of a laser diode LD serving as a beam source for radiation (43a in FIG. 1). And, the time between one pulse and its next pulse in the vertical scan signal VD shown in FIG. 6 represents the period of 1 screen (1 frame).

In the case of an ordinary image sensor of a CMOS type which is a rolling shutter system, since there is no element which can hold simultaneously signal charges generated at the respective pixel positions of the photoelectric conversion portion of the imaging device for all pixels, it is necessary to perform the charge accumulation and signal charge read-out sequentially on every line of a large number of pixel groups arranged in the line and row directions.

In this case, as shown in FIG. 6, the timing of the electronic shutter pulses to be applied to the imaging device 11b is shifted slightly in every scan line (every line of the pixel groups). For example, in the first scan line L1, the electronic shutter pulse opens the shutter at the time t11 and closes the shutter at the time t21, whereas, in the n-th scan line Ln, the electronic shutter pulse opens the shutter at the time t1n and closes the shutter at the time t2n. That is, the shutter-opening time t1n and shutter-closing time t2n of the n-th scan line Ln are delayed in timing by the time Tc1 and time Tc2 respectively with respect to the first scan line L1. The period from the time when the electronic shutter is opened to the time when it is closed (for example, in FIG. 6, "Tc1+Tb1"), that is, the lengths of the charge accumulation periods of the respective pixel positions are the same in all scan lines.

For example, as shown in FIG. 6, in the case that the charge accumulation periods of the respective pixel positions are equal to the period of 1 frame (an interval between the pulses of the vertical scan signal VD), at any timing, when the beam source of radiation is turned off, its influence appears as a variation in the charge accumulation periods of the respective pixel positions of the imaging device 11b. Also, since the charge accumulation periods are shifted in the timing in every line, according to the timing at which the beam source of radiation is turned off, different influences appear in each of the lines of the imaging device 11b.

Therefore, in the example shown in FIG. 6, the drive signal SLD of the laser diode LD for radiation is controlled in such a manner that the beam source can be turned on substantially continuously. Thus, in the example shown in FIG. 6, although the above-mentioned pulse number modulation (PNM) control is not performed, the pulse width modulation (PWM) control, pulse amplitude modulation (PAM) control and pulse density modulation (PDM) control are performed.

That is, even during the period (whole period) during which the beam source is on, lighting and lighting-out are cyclically repeated at a very short cycle, thereby controlling the drive signal SLD to blink the beam source. In other words, during the lighting cycle Td from the time t31 to the time t32 shown, the lighting and lighting-out of the beam source drive signal SLD are controlled to lighting and lighting-out, thereby adjusting the width of a pulse expressing the time for actually lighting the beam source. The beam quantity (blinking ratio) is controlled in this manner. This is PWM control.

Also, the lighting cycle Td that is used in PWM control is not constant but is variable. The control that adjusts the lighting cycle Td is PDM control. That is, even in the case that the pulse width (lighting period Te) in the lighting cycle Td is constant, when the lighting cycle Td elongates, the beam quantity for radiation decreases; and, when the lighting cycle Td is shorten, the beam quantity for radiation increases. Also, in the case that the width of the pulse of the beam source drive signal SLD is set variable, the intensity (instantaneous value) of a current to be applied to the beam source can be changed, thereby being able to adjust the on intensity of the beam source. This is PAM control.

Also, the on cycle Td used in the PWM control is not constant but is variable. The control for controlling the on cycle Td is PDM control. That is, even in the case that the pulse width (on period Te) in the on cycle Td is constant, when the on cycle Td increases, the beam quantity for radiation decreases; and, when the on cycle Td decreases, the beam quantity for radiation increases. Also, in the case that the amplitude of the pulse of the beam source drive signal SLD is set variable, the intensity (instantaneous value) of the current to be applied to the beam source can be changed and thus the on intensity of the beam source can be controlled. This is PAM control.

In the example shown in FIG. 6, the beam source drive signal SLD is controlled in such a manner that the beam source for radiation can be turned on continuously. However, alternatively, for example, the beam source for radiation may be turned on only during the period Tb shown in FIG. 6 and may be turned off during the remaining periods. That is, while avoiding the periods (the respective periods Tc1, Tc2) for switching the lines in the rolling shutter control of the imaging device 11b, the beam source may be turned on in the range of other periods, that is, in the range of the common accumulation period (Tb) during which all lines of 1 frame are turned into their respective charge accumulation states simultaneously. In this case, even in the case of the rolling shutter control, the lengths of the actual exposure times (charge accumulation periods) of the respective lines can be made to coincide with each other and thus the above-mentioned pulse number modulation (PNM) control can also be performed. In other words, without paying attention to the timing for switching the lines in the rolling shutter control, the beam quantity for radiation can be controlled. Therefore, as far as the control in the range of the common accumulation period (Tb) is concerned, PNM control can also be added to the beam source driver 43b including LUT 101B shown in FIG. 4.

The control unit 13 shown in FIG. 1 uses a beam control table in order to control the beam quantity of the beam source 43a. This beam control table represents the relationship between a beam quantity specified value for controlling the beam quantity of the beam source 43a and a control output value; and, the beam control table is provided, for example, in LUT 101A and LUT 101B respectively shown in FIG. 4. The control output value of the beam control table is set as any one of a control value for PAM control, a control value for PWM control and a control value for PDM control, or multiple combinations of these control values.

In order to carry out proper beam quantity control, it is necessary to use a proper beam control table. For example, a case where the endoscope 11 to be connected to the beam source apparatus 43 mounts thereon a CCD image sensor as an imaging device and a case where the endoscope 11 mounts a CMOS image sensor are different in the proper control conditions from each other. Therefore, in the respective cases, there must be used mutually different beam control tables.

Figure 7:
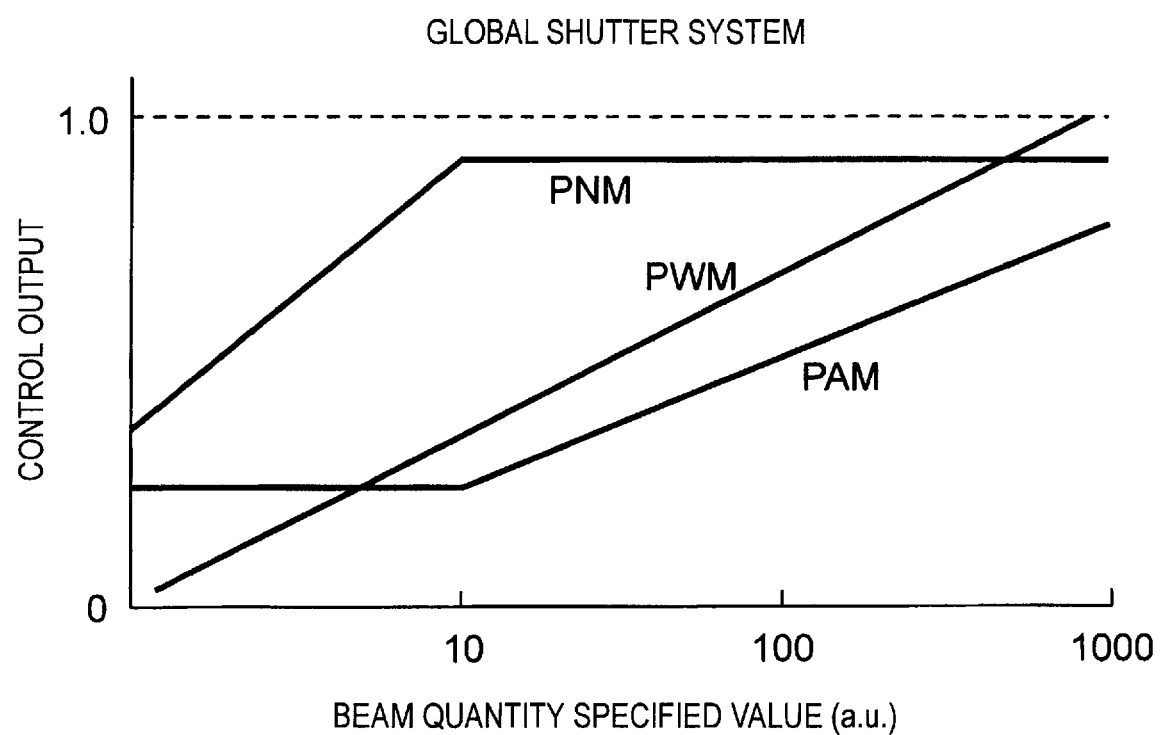
FIG. 7 is a graphical representation of an example of the properties of a control pattern relating to the operation of the beam source driver shown in FIG. 4.
Figure 8:
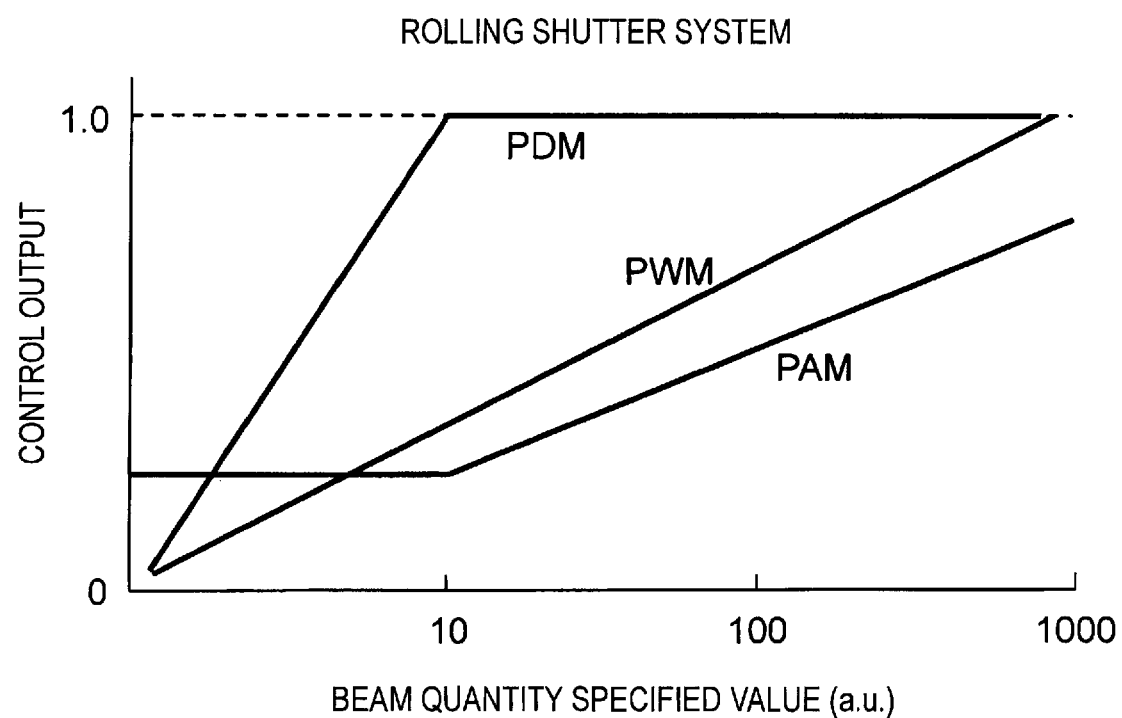
FIG. 8 is a graphical representation of an example of the properties of another control pattern relating to the operation of the beam source driver shown in FIG. 4.

FIGS. 7 and 8 respectively show the characteristics of control patterns relating to the operation of the beam source driver shown in FIG. 4. Specifically, in LUT 101A of the beam source driver shown in FIG. 4, there is provided a beam control table which represents such control pattern as shown in FIG. 7. Also, in LUT 101B of the beam source driver, there is provided a beam control table which represents such control pattern as shown in FIG. 8.

Referring to FIG. 7, this control pattern is constituted of a combination of three kinds of control characteristics, that is, the control characteristics of PNM control, the control characteristics of PWM control and the control characteristics of PAM control. In the case of the control pattern shown in FIG. 7, in the range of beam quantity specified values 1~10, there is output a PAM control value having a constant minimum amplitude and, at the same time, there is output as a variable value a PNM control value which can vary in such a manner that it can increase the beam quantity with an increase in the beam quantity specified value. When the beam quantity specified value exceeds 10, with an increase in the specified value, the PAM control value increases, while the PNM control value becomes a constant value. The PWM control value varies over the entire area of the beam quantity specified values 0~1000 in such a manner that it increases the beam quantity with an increase in the beam quantity specified value. That is, in the case that there is employed the control pattern shown in FIG. 7, due to the combination of the control outputs of the PNM control, PWM control and PAM control, the current to be applied to the beam source, that is, the beam quantity of the beam source can be determined.

Referring to FIG. 8, this control pattern is constituted of a combination of three kinds of control characteristics, that is, the control characteristics of PDM control, the control characteristics of PWM control and the control characteristics of PAM control. In the case of the control pattern shown in FIG. 8, in the range of beam quantity specified values 1~10, there is output a PAM control value having a constant minimum amplitude and, at the same time, there is output as a variable value a PDM control value which can vary in such a manner that it can increase the beam quantity with an increase in the beam quantity specified value. When the beam quantity specified value exceeds 10, with an increase in the specified value, the PAM control value increases, while the PDM control value becomes a maximum value (a constant value). The PWM control value varies over the entire area of the beam quantity specified values 0~1000 in such a manner that it increases the beam quantity with an increase in the beam quantity specified value. That is, in the case that there is employed the control pattern shown in FIG. 8, due to the combination of the control outputs of the PDM control, PWM control and PAM control, the current to be applied to the beam source, that is, the beam quantity of the beam source can be determined.

In the case that the beam source apparatus 43 is designed assuming that the endoscope 11 to be connected thereto is an imaging device such as a CCD image sensor which is controlled according to a global shutter system, there are previously determined the contents of a beam control table in such a manner that the beam source driver 43b of this beam source apparatus 43 can provide such a control pattern as shown in FIG. 7.

Also, in the case that the beam source apparatus 43 is designed assuming that the endoscope 11 to be connected thereto is a CCD image sensor which is controlled according to a rolling shutter system, there are previously determined the contents of a beam control table in such a manner that the beam source driver 43b of this beam source apparatus 43 can provide such a control pattern as shown in FIG. 8.

In the case that the imaging device 11b of the endoscope 11 is a CCD image sensor, periods during which the electric shutter is opened are common in all pixels. Also, the radiation beam while the electric shutter is closed is not used for photographing but can lead to heat generation in the leading end portion of the endoscope 11 and a portion to be observed. Therefore, in such situation, preferably, at least PNM control may be performed to lighting-out the beam source for radiation while the electric shutter is closed. And, in this situation, PDM control is not suitable, because it turns on the beam source successively regardless of the timing for opening and closing the electronic shutter.

On the other hand, in the case that the imaging device 11b of the endoscope 11 is a CMOS image sensor of a rolling shutter system, periods during which the electronic shutter is open vary little by little in every line of pixel groups. Therefore, in this case, in order to prevent the beam quantity for radiation from varying in every line, it is necessary to allow the beam source for radiation to emit a beam successively. That is, PNM control is not suitable but, preferably, the beam quantity may be controlled using PDM control.

As described above, according to the present endoscope system 100, the beam source driver 43b of the control unit 13 can control the beam quantity integrally by combining together three or more of the lighting intensity, lighting rate, lighting time and lighting density of the beam source 43a. Thanks to this, a user, simply by controlling a beam quantity specified value, can control the respective control values of the lighting intensity, lighting ratio, lighting time and lighting density of the beam source 43a in order that the beam quantity for radiation can provide a proper quantity. This can facilitate the operation of the endoscope system 100. Also, by combining the multiple kinds of control, the dynamic range of the beam control can be enlarged.

Figure 9:
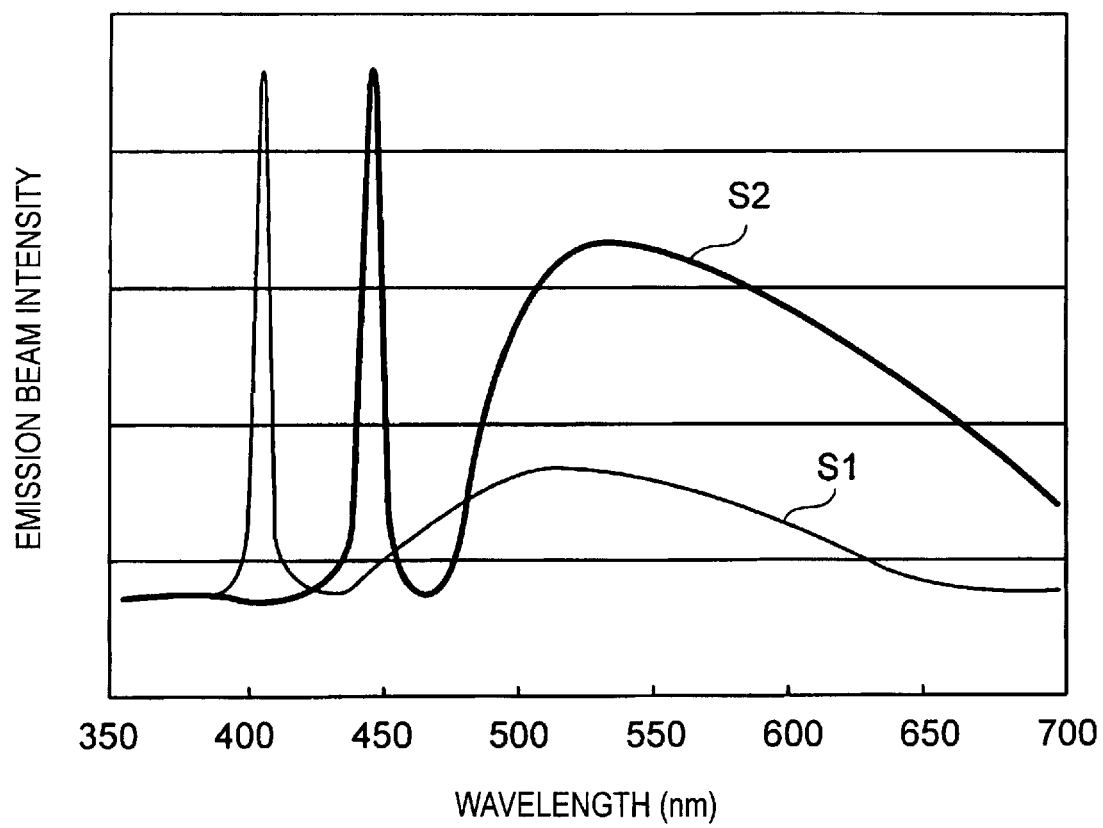
FIG. 9 is a graphical representation of a specific example of the spectrum of a radiation beam.

FIG. 9 shows a specific example of the spectra of the beam used for radiation in the endoscope system 100. A spectrum S1 shown in FIG. 9 represents a beam emission intensity distribution of such radiation beam by wavelengths as is radiated onto the portion to be observed of a living body or the like from the endoscope leading end portion 35 when a laser beam source having a center wavelength of 405 nm is employed as the beam source 43a. Also, a spectrum S2 represents a beam emission intensity distribution of such radiation beam by wavelengths as is radiated onto the portion to be observed of a living body or the like from the endoscope leading end portion 35 when a laser beam source having a center wavelength of 445 nm is employed as the beam source 43a.

For example, a laser beam of 445 nm, which is a blue beam, is emitted from the beam source 43a; and, this blue beam is guided to the radiation unit 11a of the endoscope 11 and is radiated onto the fluorescent member 72. In this case, part of the blue beam is absorbed by the fluorescent member 72 and the fluorescent member 72 is thereby excited to emit a beam. The beam emitted from the fluorescent member 72 is a visible beam having a wavelength band ranging from green to yellow. And, the remaining energy component of the blue beam, which is not absorbed by the fluorescent member 72 but is transmitted therethrough, and the beam emitted due to the excitation of the fluorescent member 72 are added together; and, the thus added beam is radiated onto the portion to be observed from the endoscope leading end portion 35 as a white radiation beam having such a wavelength distribution as the spectrum S2 shown in FIG. 9.

Similarly, when a laser beam of 405 nm is emitted by the beam source 43*a*, this laser beam is guided to the radiation unit 11*a* of the endoscope 11 and is then radiated onto the fluorescent member 72, this laser beam is radiated onto the portion to be observed from the endoscope leading end portion 35 as a radiation beam having such a wavelength distribution as the spectrum S1 shown in FIG. 9.

Next, description will be given below of several modifications of the radiation beam of the endoscope system 100.

Figure 10:
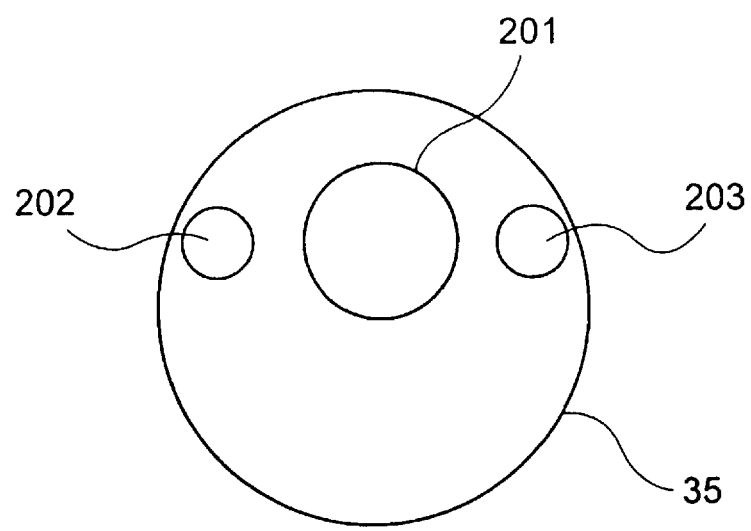
FIG. 10 is a front view of the structure of an endoscope leading end portion according to a first modification.

FIG. 10 is a structure view of the endoscope leading end portion 35 according to a first modification, that is, FIG. 10 shows that a state in which the leading end side end face thereof is viewed from the portion to be observed. Also, FIG. 11 is a block diagram of the structure of a beam source apparatus 43 according to the first modification.

In the example shown in FIG. 10, in the endoscope leading end portion 35, there are formed one observation window 201 and two illumination windows 202 and 203 respectively disposed on both sides of the observation window 201. In the case that the two illumination windows 202 and 203 are disposed on both sides of the observation window 201 in this manner and radiation beams are respectively emitted from the two illumination windows 202 and 203, uneven radiation is hard to occur in an observation image; and, when a treating device is inserted through a forceps hole and is projected from the endoscope leading end, it is possible to prevent the treating device from showing its shadow in the observation image, and a sufficient beam quantity can be obtained over a wide range.

Figure 11:
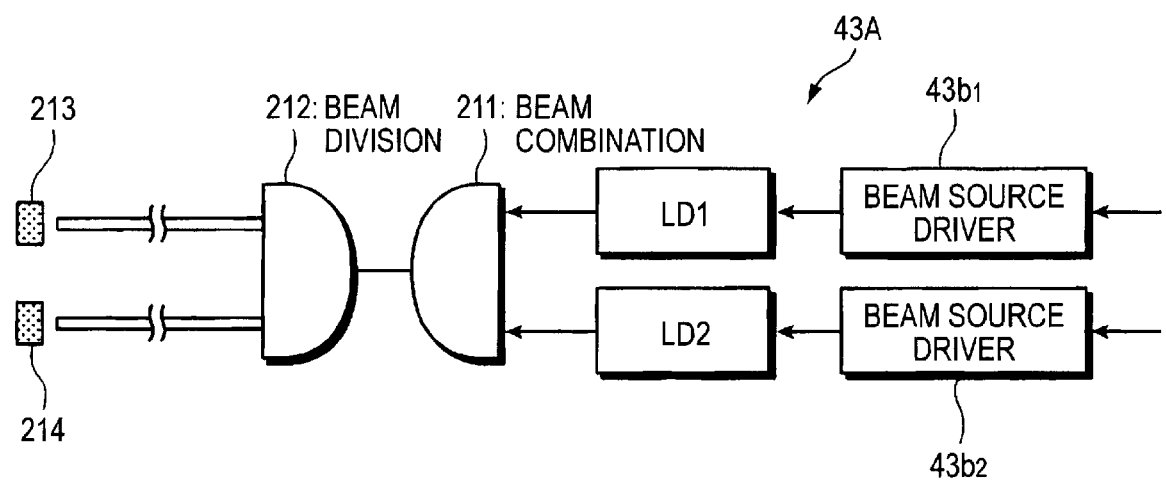
FIG. 11 is a block diagram of the structure of a beam source apparatus according to the first modification.

When the endoscope 11 shown in FIG. 10 is used, as the beam source 43, there is used, for example, a beam source apparatus 43A having such structure as shown in FIG. 11. The beam source apparatus 43A shown in FIG. 11 includes a laser beam source LD1 having a center wavelength of 445 nm and a laser beam source LD2 having a center wavelength of 405 nm.

The two laser beam sources LD1 and LD2 are respectively connected to two independent beam source drivers 43*b*1 and 43*b*2, while the emission beam quantities thereof are controlled individually. The emission beams of the two laser beam sources LD1 and LD2 are combined together by a combiner 211, while the combined beams are divided by a coupler 212 to multiple optical paths and are then radiated onto fluorescent members 213 and 214 respectively disposed in the beam emission ends of the respective optical paths.

Of the two laser beam sources LD1 and LD2, when only the laser beam source LD1 is turned on, there is emitted a white radiation beam for normal observation as a radiation beam. That is, the emission beams of the fluorescent members 213 and 214 generated due to the excitation of the fluorescent members 213 and 214 caused by the radiation of a laser beam having a center wavelength of 445 nm and the laser beam having a center wavelength of 445 nm transmitted through the fluorescent members 213 and 214 are added together, thereby providing a radiation beam having a spectrum near white.

Also, in the case that the two laser beam sources are turned on synchronously at such beam quantity ratio that LD1:LD2 is about 1:7, there can be obtained an observation image which is observed by a radiation beam for narrow bandwidth beam observation and in which fine blood vessels existing in the tissue surface layer are emphasized. Further, in the case that the two laser beam sources are turned on synchronously at such beam quantity ratio that LD1:LD2 is about 4:1, there can be obtained a hybrid radiation beam constituted of a white beam and a narrow bandwidth beam. According to this hybrid radiation beam, there can be obtained an observation image constituted of a normal observation image with information about the fine blood vessels of the tissue surface layer superimposed thereon.

Due to use of the two laser beam sources LD1 and LD2, there can be obtained a radiation beam having such spectra S1 and S2 as shown in FIG. 9. Also, in the case that a blue laser beam having a center wavelength of 445 nm and a violet laser beam having a center wavelength of 405 nm are emitted synchronously and are combined together, a wavelength band beam of about 460~470 nm, which is short in the blue laser beam having a center wavelength of 445 nm, can be compensated by a beam in the same band width which is emitted from the violet laser beam having a center wavelength of 405 nm, thereby being able to improve the color tone (color rendering properties) of the white beam.

Figure 12:
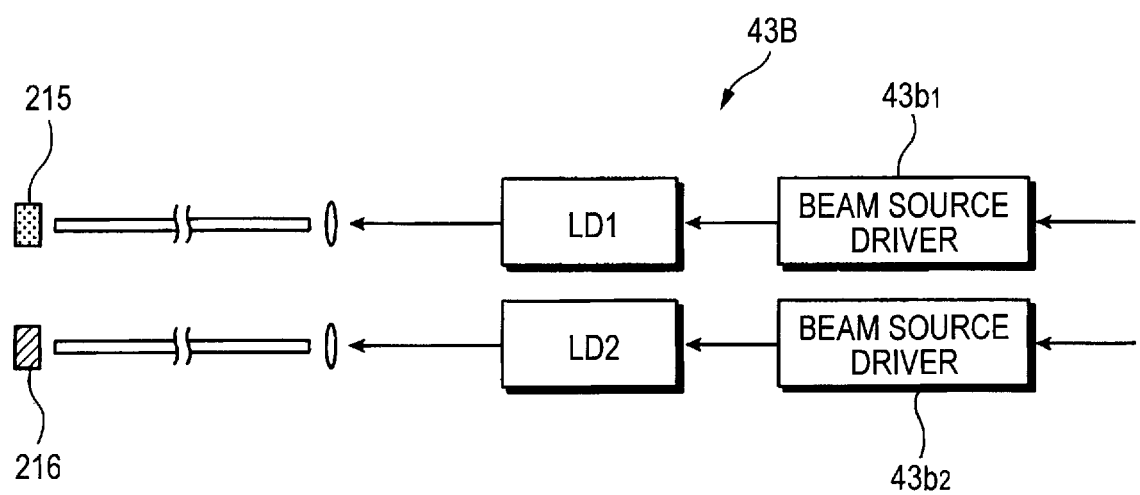
FIG. 12 is a block diagram of the structure of a beam source apparatus according to a second modification.

FIG. 12 shows the structure of the beam source apparatus 43 according to a second modification. In the case that the radiation beam can be emitted from the plural systems of illumination windows as shown in FIG. 10, for example, using the beam source apparatus 43B shown in FIG. 12, there may also be emitted from the plural systems of illumination windows beams which are different in spectrum from each other.

The beam source apparatus 43B shown in FIG. 12, similarly to the beam source apparatus 43A, includes a laser beam source LD1 having a center wavelength of 445 nm and a laser beam source having a center wavelength of 405 nm. The beams emitted from the laser beam sources LD1 and LD2 are not combined or divided. The emission beam of the laser beam source LD1 is at it is radiated onto a fluorescent member 215, while the emission beam of the laser beam source LD2 is guided through a diffusion member 216 to the illumination window. In this case, since the laser beam having a center wavelength of 405 nm can be radiated not through the fluorescent member, it can be used as a radiation beam while it remains as a narrow bandwidth beam. Thus, when carrying out a fluorescence observation or the like using an endoscope, there can be obtained an image which includes few noises.

Figure 13:
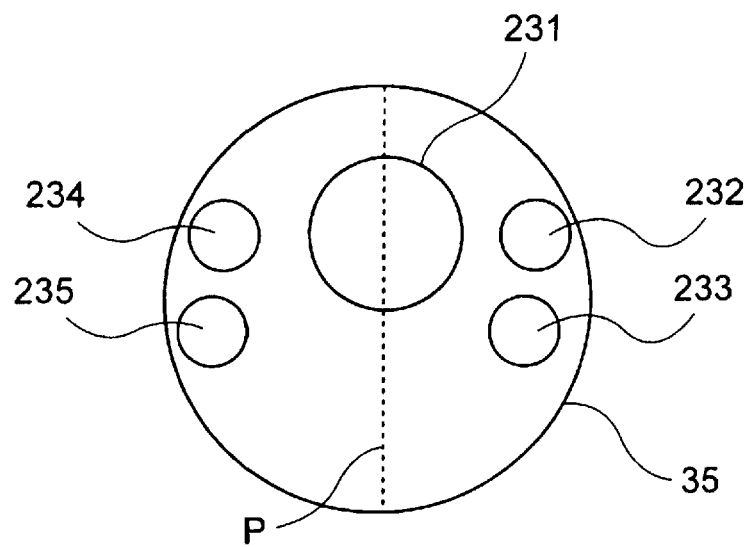
FIG. 13 is a front view of the structure of an endoscope leading end portion according to a third modification.

FIG. 13 is a structure view of an endoscope leading end portion 35 according to a third modification, that is, FIG. 13 shows that a state in which the leading end side end face of the endoscope leading end portion 35 is viewed from the portion to be observed. Also, FIG. 14 is a block diagram of the structure of a beam source apparatus 43 according to the third modification.

According to the example shown in FIG. 13, in the endoscope leading end portion 35, there are formed one observation window 231 and two pairs of illumination windows (232, 233, 234 and 235) respectively disposed on both sides of the observation window 231. In the example shown in FIG. 13, the illumination windows 232 and 235 come as a pair, while the illumination windows 233 and 234 come as a pair. And, there is employed a structure in which, from the paired two illumination windows, there are emitted the same kinds of radiation beams. Due to use of the two pairs of illumination windows, there can be emitted synchronously beams which are different in spectrum from each other. That is, from one pair of illumination windows, there are emitted radiation beams respectively having a first spectrum; and, from the other pair of illumination windows, there are emitted radiation beams respectively having a second spectrum.

Here, the two pairs of illumination windows to be formed on both sides of the observation window are structured in the following manner. That is, while a straight line passing through the center point of the observation window and bisecting the leading end face of the insertion portion leading end is used as a boundary line P, the paired illumination windows are respectively disposed such that they stride over the boundary line P, one pair of first illumination windows (232 and 235) can serve as illumination windows for radiating a white beam, and the other pair of second illumination windows (233 and 234) can serve as illumination windows for radiating a narrow bandwidth beam which is narrower than the white beam.

Figure 14:
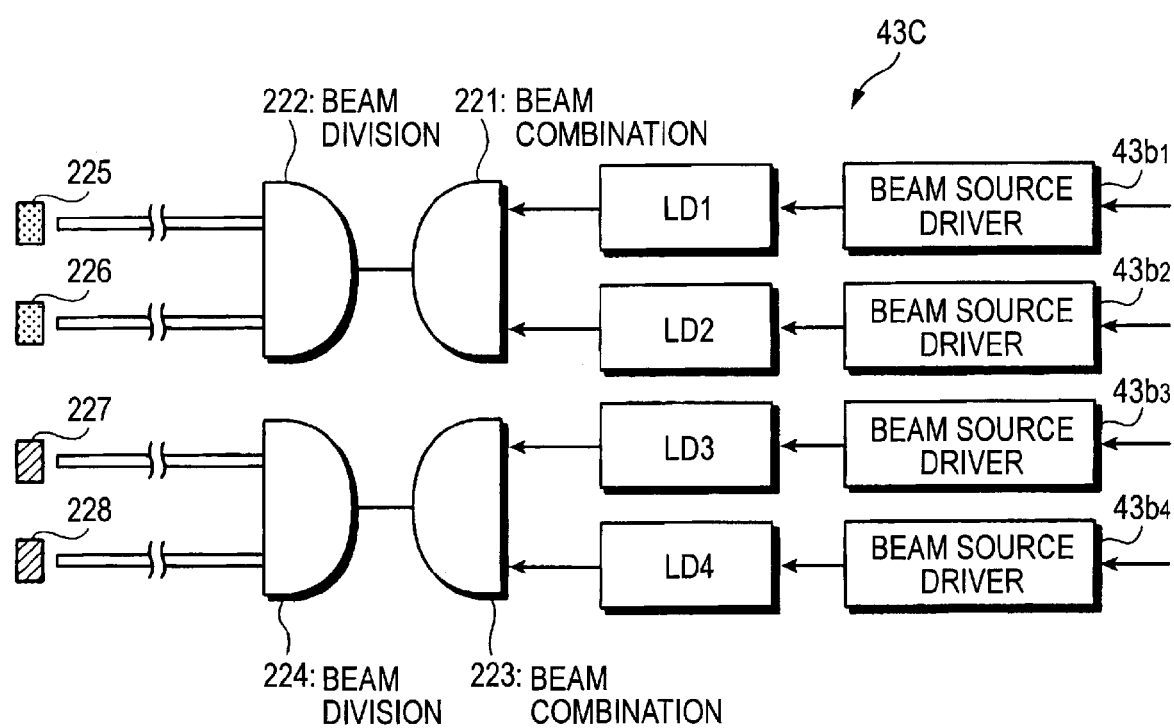
FIG. 14 is a block diagram of the structure of a beam source apparatus according to the third modification.

In the case that there is used the endoscope 11 shown in FIG. 13, as the beam source apparatus 43, there is used, for example, a beam source apparatus 43C having such a structure as shown in FIG. 14. The beam source apparatus 43C shown in FIG. 14 includes a laser beam source LD1 having a center wavelength of 445 nm, a laser beam source LD2 having a center wavelength of 405 nm, a laser beam source LD3 having a center wavelength of 472 nm and a laser beam source LD4 having a center wavelength of 780 nm.

The four laser beam sources LD1, LD2, LD3 and LD4 are respectively connected to their associated independent beam source drivers 43b1, 43b2, 43b3 and 43b4, while the emission beam quantities thereof can be controlled individually. The emission beams of the two laser beam sources LD1 and LD2 are combined together by a combiner 221, are divided to two optical paths by a coupler 222, and are radiated onto fluorescent members 225 and 226 respectively disposed on the beam emission ends of the respective optical paths. Also, the emission beams of the remaining two laser beam sources LD3 and LD4 are combined together by a combiner 223, are divided by a coupler 224 to two optical paths, and are guided to the illumination windows through diffusion members 227 and 228 respectively disposed on the beam emission ends of the respective optical paths.

According to the third modification having the structure shown in FIGS. 13 and 14, when LDs respectively having center wavelengths of 405 nm, 445 nm and 472 nm are turned on sequentially and the images of the portion to be observed are picked up, there can be extracted information about oxygen saturation from the observed image. Specifically, using a difference between the absorbance spectra of oxygenated hemoglobin $HbO_2$ and reduced hemoglobin Hb after release of oxygen respectively included in hemoglobin contained in an erythrocyte existing in blood, there can be obtained the oxygen saturation and blood depth of the observation area. Oxygenated hemoglobin $HbO_2$ and reduced hemoglobin Hb are substantially equal in the absorbance in the vicinity of a wavelength of 405 nm; in the vicinity of a wavelength of 445 nm, reduced hemoglobin Hb is higher in the absorbance than oxygenated hemoglobin $HbO_2$; and, in the vicinity of a wavelength of 472 nm, oxygenated hemoglobin $HbO_2$ is higher in the absorbance than reduced hemoglobin Hb. Also, a laser beam has such properties that the shorter the wavelength of the laser beam is, the shallower the reaching depth of the laser beam from the mucous tissue surface layer is. Using these properties, there can be obtained the oxygen saturation of the observation area and the blood depth that is projected on the observation area.

The laser beam having a center wavelength of 785 can be used properly to observe the blood information of the mucous tissue deep layer, thereby being able to perform an infrared beam observation using ICG (indocyanine green) and blood vessel navigation. This ICG, when in blood, provides a state in which it is connected to protein, absorbs a near infrared beam having a wavelength of, for example, 750–850 nm while the maximum absorbing wavelength is 805 nm, and emits near infrared fluorescence.

According to this radiation pattern, since there can be radiated a near infrared beam in addition to a white beam, there can be extracted, especially, the blood vessel information of the mucous tissue deep layer which is hard to obtain by a visible beam. For example, in the case that this beam projection unit is applied to an endoscope navigation system for obtaining information about the position of blood vessels existing around a bronchial tube, a laser beam having a center wavelength of 785 nm is radiated toward ICG charged into the blood vessels. In this case, in a portion where blood and ICG react with each other, there is emitted fluorescence having broad spectral characteristics and having a peak wavelength of 830 nm. By using the thus emitted fluorescence as a mark, the position accuracy can be enhanced and thus accurate treatment can be performed. Further, since there are used multiple beam projection units, by combining together beams from the respective beam projection units, beam radiation of high intensity can be realized.

Further, as the laser beam sources LD3 and LD4, there may also be used laser beam sources which can emit laser beams respectively having center wavelengths of 375 nm, 405 nm, 445 nm and the like. The laser beam having a wavelength of 375 nm provides an excitation beam when a fluorescent observation is performed using "luciferase" which is one of fluorescent medicines. Also, since the laser beams having the wavelengths of 405 nm and 445 nm can be radiated without passing through the fluorescent member, they can be radiated while they remain as the narrow bandwidth beams.

Although description has been given heretofore of the embodiment according to the invention, the invention is not limited to the embodiment. But, the invention also suggests that a person skilled in the art can make a change in the invention and apply the change to other similar system. Of course, such change falls under the scope of the invention.
As described above, the present description discloses the following contents.

(1) An endoscope beam source apparatus is connected to an endoscope. The endoscope mounts a radiation optical system for radiating a beam onto a subject and an imaging optical system including an imaging device for imaging an image of the subject. The endoscope beam source apparatus includes a beam source and a beam source control unit. The beam source emits radiation beam to be supplied to the endoscope. The beam source control unit controls emission beam intensity of the beam source according to a beam quantity specified value input therein. The beam source control unit specifies the emission beam intensity of the beam source corresponding to the beam quantity specified value based on at least three of control amounts. The control amounts include a control amount corresponding to pulse number modulation control for changing lighting time of the beam source, a control amount corresponding to pulse width modulation control for changing a pulse width which indicates the lighting time or lighting-out time within a control cycle, a control amount corresponding to pulse amplitude modulation control for changing lighting intensity, and a control amount corresponding to pulse density modulation control for changing a lighting interval.

According to the present endoscope beam source apparatus, since the combinations of three or more kinds of modulation control are integrated to perform the control of the beam quantity, a large beam quantity dynamic range of about 1:9000 can be obtained easily. Also, since the respective control amounts of three or more kinds of modulation control can be controlled simply by operating a beam quantity specified value to be provided to the beam source control unit, an operation for a user to control the beam of the beam source can be simplified greatly.

(2) The endoscope beam source apparatus according to (1), the imaging device mounted on the endoscope to be connected to the endoscope beam source apparatus is specified to a imaging device to be controlled according to a global shutter system. The beam source control unit specifies the emission beam intensity of the beam source based on a combination of the control amount corresponding to the pulse number modulation control, the control amount corresponding to the pulse width modulation control and the control amount corresponding to the pulse amplitude modulation control.

According to the present endoscope beam source apparatus, in the case that there is connected thereto an endoscope on which an imaging device such as a CCD image sensor is mounted, it is possible to perform desired beam control suitable for this imaging device.

(3) The endoscope beam source apparatus according to (2), the beam source control unit controls lighting of the beam source within a charge accumulation period per one frame of the imaging device by using time of a predetermined rate or more therethan of the charge accumulation period.

According to the present endoscope beam source apparatus, even in the case that the length of the charge accumulation period corresponding to the electronic shutter speed is constant, the exposure quantity can be adjusted by controlling the beam of the beam source and thus the brightness of an image to be picked up can be adjusted. Also, by limiting the lighting time such that it can provide a predetermined rate of the charge accumulation time or higher, an equivalent increase in the electronic shutter speed can be prevented. Therefore, the photographing conditions can be controlled independently using the exposure quantity due to the control of the beam for radiation and the degree of shaking of the imaging device to be determined by the electronic shutter speed, thereby being able to facilitate the determination of the photographing conditions. For example, in the case that the above-mentioned predetermined rate is set for 1/2, in the reproduction of moving images, there can be prevented a feeling of discontinuity and also the flickering of the moving images.

(4) The endoscope beam source apparatus according to (2) or (3), when the beam quantity specified value is a predetermined value or larger therethan, the beam source control unit controls the control amount corresponding to the pulse number modulation control as a maximum constant value. When the beam quantity specified value is less than the predetermined value, the beam source control unit controls the control amount corresponding to the pulse number modulation control as a variable value which decreases as the beam quantity specified value decreases.

According to this endoscope beam source apparatus, since the relationship between a variation in the beam quantity specified value and a substantial radiation beam quantity can be obtained similarly to an ordinary beam source apparatus which controls the above relationship simply by controlling only the lighting intensity (amplitude) thereof, compatibility between the present beam source apparatus and ordinary beam source apparatus can be secured. That is, even in the case that an endoscope beam source apparatus is changed from a conventional apparatus to the apparatus according to the invention, there is no possibility that a user can have a strange feeling. Also, in the case that the beam quantity specified value is less than a predetermined value, by reducing the control amount of the pulse number modulation control, the exposure period can be made sufficiently short when compared with the charge accumulation period. Therefore, when the beam quantity specified value is small as in a case where the scope leading end of an endoscope is put close to the portion to be observed to pick up a static image, there can be reduced a blur which can be caused to appear in the static image to be picked up.

(5) The endoscope beam source apparatus according to (1), the imaging device mounted on the endoscope to be connected to the endoscope beam source apparatus is specified to a imaging device to be controlled according to a rolling shutter system. The beam source control unit specifies the emission beam intensity of the beam source according to a combination of the control amount corresponding to the pulse density modulation control, the control amount corresponding to the pulse width modulation control and the control amount corresponding to the pulse amplitude modulation control.

According to this endoscope beam source apparatus, in the case that there is connected thereto an endoscope on which an imaging device such as an ordinary CMOS image sensor is mounted, it is possible to perform desired beam control suitable for this imaging device.

(6) The endoscope beam source apparatus according to (5), the imaging device includes a plurality of independent photoelectric conversion portions in every pixel arranged in line and row directions. The respective pieces of control for accumulating charges into the respective photoelectric conversion portions and control for reading out the accumulated charges are performed at the respective pieces of timing mutually differing from each other in every line of the respective photoelectric conversion portions. The beam source control unit controls lighting of the beam source in a range of a common accumulation period representing timing at which all lines of one frame are simultaneously in their charge accumulating states. The common accumulation period is contained in the charge accumulation periods of the respective lines of the imaging device.

According to this endoscope beam source apparatus, in the case that there is connected thereto an endoscope mounting thereon an imaging device such as a CMOS image sensor, the photoelectric conversion portions of the imaging device at any pixel positions are influenced by the same radiation beam quantity due to control of the beam source. Therefore, it is possible to prevent the brightness of an image to be picked up from being uneven.

(7) The endoscope beam source apparatus according to (5) or (6), when the beam quantity specified value is a predetermined value or larger therethan, the beam source control unit controls the control amount corresponding to the pulse density modulation control as a maximum constant value and. When the beam quantity specified value is less than the predetermined value, the beam source control unit controls the control amount corresponding to the pulse density modulation control as a variable value which decreases as the beam quantity specified value decreases.

According to this endoscope beam source apparatus, since the relationship between a variation in the beam quantity specified value and a substantial radiation beam quantity can be obtained similarly to an ordinary beam source apparatus which controls the above relationship simply by controlling only the lighting intensity (amplitude) thereof, compatibility between the present beam source apparatus and ordinary beam source apparatus can be secured. That is, even in the case that an endoscope beam source apparatus is changed from a conventional apparatus to the apparatus according to the invention, there is no possibility that a user can have a strange feeling.

(8) An endoscope system includes an endoscope beam source apparatus according to any one of (1) to (7) and an endoscope. The endoscope is connected to the endoscope beam source apparatus. The radiation optical system contained in the endoscope includes an optical fiber and a fluorescent member. The optical fiber guides the beam emitted from the beam source. The fluorescent member is disposed forwardly in an optical path of a beam emitting end of the optical fiber. The radiation optical system mixes together the beam emitted from the beam source and the beam emitted from the fluorescent member to generate a radiation beam.

According to this endoscope system, even without using a xenon lamp or a metal halide lamp as a beam source, by using a light emitting diode or a semiconductor laser diode, there can be obtained a radiation beam having a spectrum near a white beam. This makes it possible to reduce the size and cost of the present system.

(9) An endoscope system includes an endoscope beam source apparatus according to any one of (1) to (7) and a plurality of beam sources. The plurality of beam sources emits beams respectively having mutually different spectra. The beam source control unit controls the plurality of beam sources respectively.

According to this endoscope system, since multiple radiation beams respectively having different spectra can be used selectively, the present system is able to cope with various observation modes.

(10) An endoscope system including an endoscope beam source apparatus according to any one of (1) to (7), the beam source is constituted of a semiconductor light emitting element.

According to this endoscope system, since there is used a semiconductor light emitting element as a beam source, the size and cost of the present system can be reduced.

What is claimed is:

1. An endoscope beam source apparatus which is connected to an endoscope, the endoscope mounting a radiation optical system for radiating a beam onto a subject and an imaging optical system including an imaging device for imaging an image of the subject, the endoscope beam source apparatus comprising:
    a beam source that emits radiation beam to be supplied to the endoscope; and
    a beam source control unit that controls emission beam intensity of the beam source according to a beam quantity specified value input therein,
    wherein the beam source control unit specifies the emission beam intensity of the beam source corresponding to the beam quantity specified value based on at least three of control amounts,
    the control amounts include:
        a control amount corresponding to pulse number modulation control for changing lighting time of the beam source;
        a control amount corresponding to pulse width modulation control for changing a pulse width which indicates the lighting time or lighting-out time within a control cycle;
        a control amount corresponding to pulse amplitude modulation control for changing lighting intensity; and
        a control amount corresponding to pulse density modulation control for changing a lighting interval,
    the imaging device mounted on the endoscope to be connected to the endoscope beam source apparatus is specified to a imaging device to be controlled according to a global shutter system, and
    the beam source control unit specifies the emission beam intensity of the beam source based on a combination of the control amount corresponding to the pulse number modulation control, the control amount corresponding to the pulse width modulation control and the control amount corresponding to the pulse amplitude modulation control.

2. The endoscope beam source apparatus according to claim 1, wherein the beam source control unit controls lighting of the beam source within a charge accumulation period per one frame of the imaging device by using time of a predetermined rate or more therethan of the charge accumulation period.

3. The endoscope beam source apparatus according to claim 1, wherein, when the beam quantity specified value is a predetermined value or larger therethan, the beam source control unit controls the control amount corresponding to the pulse number modulation control as a maximum constant value and, when the beam quantity specified value is less than the predetermined value, the beam source control unit controls the control amount corresponding to the pulse number modulation control as a variable value which decreases as the beam quantity specified value decreases.

4. An endoscope system comprising:
    an endoscope beam source apparatus according to claim 1; and
    an endoscope that is connected to the endoscope beam source apparatus,
    wherein the radiation optical system contained in the endoscope includes:
        an optical fiber which guides the beam emitted from the beam source; and
        a fluorescent member which is disposed forwardly in an optical path of a beam emitting end of the optical fiber, and
    the radiation optical system mixes together the beam emitted from the beam source and the beam emitted from the fluorescent member to generate a radiation beam.

5. An endoscope system comprising:
    an endoscope beam source apparatus according to claim 1; and
    a plurality of beam sources that emit beams respectively having mutually different spectra,
    wherein the beam source control unit controls the plurality of beam sources respectively.

6. An endoscope system comprising: an endoscope beam source apparatus according to claim 1,
    wherein the beam source is constituted of a semiconductor light emitting element.

* * * * *